US009808172B2

(12) United States Patent
Marcarian

(10) Patent No.: US 9,808,172 B2
(45) Date of Patent: Nov. 7, 2017

(54) SYSTEMS AND METHODS FOR PERFORMING SURFACE ELECTROMYOGRAPHY AND RANGE-OF-MOTION TEST

(75) Inventor: David Marcarian, Seattle, WA (US)

(73) Assignee: Precision Biometrics, Inc., Seattle, WA (US)

(*) Notice: Subject to any disclaimer, the term of this patent is extended or adjusted under 35 U.S.C. 154(b) by 328 days.

(21) Appl. No.: 12/455,385

(22) Filed: Jun. 1, 2009

(65) Prior Publication Data

US 2009/0299210 A1 Dec. 3, 2009

Related U.S. Application Data

(60) Provisional application No. 61/058,160, filed on Jun. 2, 2008.

(51) Int. Cl.
*A61B 5/0488* (2006.01)
*A61B 5/11* (2006.01)
*A61B 5/00* (2006.01)

(52) U.S. Cl.
CPC .......... *A61B 5/0488* (2013.01); *A61B 5/1121* (2013.01); *A61B 5/4561* (2013.01); *A61B 5/6823* (2013.01); *A61B 5/6825* (2013.01); *A61B 5/4528* (2013.01); *A61B 2562/0219* (2013.01)

(58) Field of Classification Search
CPC ............ A61B 5/04004; A61B 5/04012; A61B 5/0488; A61B 5/0492

(Continued)

(56) References Cited

U.S. PATENT DOCUMENTS 4,320,767 A * 3/1982 Villa-Real ...................... 600/493
4,492,029 A * 1/1985 Tanaka et al. ............. 33/366.14
(Continued)

FOREIGN PATENT DOCUMENTS

EP 1516587 A2 3/2005
JP 2002-502274 1/2002
(Continued)

OTHER PUBLICATIONS

Noromed. Aug. 23, 2011 <http://www.noromed.com> (Note: brochure published in 2002; device cleared by FDA in 2001).*
(Continued)

*Primary Examiner* — Michael C Stout
*Assistant Examiner* — Nicholas E Kolderman
(74) *Attorney, Agent, or Firm* — John W. Branch; Lowe Graham Jones PLLC

(57) ABSTRACT

A soft-tissue-injury diagnostic system for diagnosing soft tissue injury within a patient includes a set of hand-held inclinometers configured and arranged for measuring angles formed between a first inclinometer disposed in proximity to a patient joint and a second inclinometer disposed distal to the joint during controlled patient movements of the joint. A plurality of measuring electrodes are coupleable in proximity to the patient's spine along the body portion that moves along the joint. The measuring electrodes are configured and arranged for measuring action potentials along patient muscle groups during the controlled patient movements of the joint and transmitting the measured action potentials to a dynamic surface electromyograph ("sEMG") module. A hub receives and processes data from the inclinometers and the dynamic sEMG module. A visual display is configured and arranged for receiving and displaying the processed data.

20 Claims, 12 Drawing Sheets

(58) Field of Classification Search
USPC .................................... 600/549, 587, 595
See application file for complete search history.

(56) References Cited

U.S. PATENT DOCUMENTS

| | | | |
|---|---|---|---|
| 4,664,130 A | 5/1987 | Gracovetsky | |
| 5,215,100 A * | 6/1993 | Spitz ..................... | A61B 5/05 600/554 |
| 5,299,572 A | 4/1994 | Chen et al. | |
| 5,369,416 A * | 11/1994 | Haverty et al. ................ | 345/39 |
| 5,459,676 A * | 10/1995 | Livingston ................... | 700/296 |
| 5,462,065 A | 10/1995 | Cusimano | |
| 5,513,651 A | 5/1996 | Cusimano et al. | |
| 5,588,444 A | 12/1996 | Petragallo | |
| 5,758,658 A * | 6/1998 | Petragallo ..................... | 600/595 |
| 6,004,312 A * | 12/1999 | Finneran et al. .............. | 600/546 |
| 6,047,202 A * | 4/2000 | Finneran et al. .............. | 600/382 |
| 6,364,849 B1 | 4/2002 | Wilcox | |
| 6,823,212 B2 * | 11/2004 | Pinyayev ...................... | 600/547 |
| 6,856,833 B2 * | 2/2005 | Finneran et al. .............. | 600/546 |
| 7,027,633 B2 | 4/2006 | Foran et al. | |
| 7,261,693 B2 | 8/2007 | Wilcox et al. | |
| 8,059,815 B2 | 11/2011 | Lofgren et al. | |
| 8,323,190 B2 | 12/2012 | Vitiello et al. | |
| 2002/0133094 A1 | 9/2002 | Wilcox et al. | |
| 2003/0135129 A1 | 7/2003 | Cusimano et al. | |
| 2004/0236221 A1 | 11/2004 | Wilcox et al. | |
| 2005/0075578 A1 | 4/2005 | Gharib et al. | |
| 2006/0052720 A1 | 3/2006 | Ross et al. | |
| 2006/0058699 A1 | 3/2006 | Vitiello et al. | |
| 2007/0156049 A1 | 7/2007 | Wilcox et al. | |
| 2007/0167859 A1 | 7/2007 | Finneran et al. | |
| 2007/0208279 A1 | 9/2007 | Panella et al. | |
| 2009/0005709 A1 * | 1/2009 | Gagne ........................... | 600/594 |
| 2009/0281408 A1 * | 11/2009 | Lee et al. ....................... | 600/372 |
| 2010/0168593 A1 | 7/2010 | Sakoda et al. | |
| 2011/0087651 A1 | 4/2011 | Westin et al. | |
| 2012/0095779 A1 | 4/2012 | Wengrovitz et al. | |
| 2013/0182007 A1 | 7/2013 | Syeda-Mahmood et al. | |

FOREIGN PATENT DOCUMENTS

| | | |
|---|---|---|
| JP | 2002-502274 A | 1/2002 |
| JP | 2004-187736 A | 7/2004 |
| JP | 2007-518430 | 7/2007 |
| JP | 2007-518430 A | 7/2007 |
| JP | 2007-209608 A | 8/2007 |
| WO | 98/46129 | 10/1998 |
| WO | 0137728 A1 | 5/2001 |
| WO | 2005/039412 | 5/2005 |

OTHER PUBLICATIONS

"Static SEMG Testing Procedure." 2007. Spinal Resources. Aug. 23, 2011. <http://spinalresources.com/html/static_semg_testing.html>.*

European Search Report, Application No. EP 09759169, dated Oct. 15, 2012.
"MES 9000 Musculoskeletal Evaluation System," NOROMED, Mar. 2002, XP002712409 http://web.archive.org/web/20070221072403/http://www.noromed.com/myotronics_root/uploadedfiles/MES%209000%20Brocue1.pdf.
Search Report for European Patent Application No. 13181241.4-1660 dated Sep. 23, 2013.
Official Communication for Japanese Patent Application No. 2011-512562 dated Aug. 7, 2013.
International Search Report and Written Opinion for International Patent Application No. PCT/US2009/045828 dated Jan. 14, 2010.
International Preliminary Report on Patentability for International Patent Application No. PCT/US2009/045828 dated Dec. 16, 2010.
Official Communication for Australian Patent Application No. 2009256441, dated May 28, 2012.
Official Communication for Australian Patent Application No. 2009256441, dated Feb. 28, 2013.
Official Communication for Chinese Patent Application No. 200980120464.3 dated May 3, 2012.
Official Communication for Chinese Patent Application No. 200980120464.3 dated Oct. 17, 2012.
Official Communication for Chinese Patent Application No. 200980120464.3 dated May 23, 2013.
Official Communication for European Patent Application No. 09759169.7, dated May 13, 2013.
Official Communication for Korean Patent Application No. 10-2010-7029868 dated Aug. 17, 2012.
Official Communication for Korean Patent Application No. 10-2010-7029868 dated Feb. 27, 2013.
Official Communication for Korean Patent Application No. 10-2010-7029868 dated May 15, 2013.
Wimalaratna, H.S.K. et al., "Quantitative Surface EMG in the Diagnosis of Neuromuscular Disorders"; Electromyography and Clinical Neurophysiology, 2002, vol. 42, pp. 167-174.
Joines, S.M.B. et al., "Low-level Exertions of the Neck Musculature: A Study of Research Methods"; Journal of Electromyography and Kinesiology, 2006, vol. 16, pp. 485-497.
Geisser, M.E. et al., "A Meta-Analytic Review of Surface Electromyography Among Persons With Low Back Pain and Normal, Healthy Controls"; The Journal of Pain, 2005, vol. 6, No. 11, pp. 711-726.
Official Communication for Chinese Patent Application No. 200980120464.3 dated Dec. 16, 2013.
Office Communication for JP Application 2013-231408 dated Sep. 24, 2014 (4 pages).
Official Communication for U.S. Appl. No. 13/830,512 dated Jan. 28, 2015 (19 pages).
Office Communication for Korean Patent Application No. 10-2012-7027138 dated Jun. 13, 2014 (7 pages).
Office Communication for Australian Patent Application No. 2013203331 dated Jul. 14, 2014 (3 pages).
Office Communication for European Patent Application No. 13181241.4 dated Feb. 4, 2015 (3 pages).

* cited by examiner

SYSTEMS AND METHODS FOR PERFORMING SURFACE ELECTROMYOGRAPHY AND RANGE-OF-MOTION TEST

CROSS-REFERENCE TO RELATED APPLICATIONS

This application is a utility patent application based on a previously filed U.S. Provisional Patent Application, Ser. No. 61/058,160 filed on Jun. 2, 2008, the benefit of which is hereby claimed under 35 U.S.C. §119(e) and the disclosures of which are herein incorporated by reference in their entirety.

TECHNICAL FIELD

The present invention is directed to medical diagnostic instrumentation. The present invention is also directed to systems and methods for evaluating soft-tissue-injury using surface electromyography or range-of-motion testing separately or in combination with one another.

BACKGROUND

Diagnosing soft-tissue injuries (e.g., injury to tissues that connect, support, or surround structures and organs of the body including, for example, muscles, tendons, ligaments, fascia, nerves, fibrous tissue, fat, blood vessels, synovial tissues; and the like), as well as assessing pain associated with soft-tissue injury, may be difficult. Soft tissue injuries are often not viewable by the naked eye. Additionally, soft-tissue injury may be difficult (and expensive) to assess even with medical imaging techniques, such as magnetic resonance imaging, computed tomography, ultrasound, and the like.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
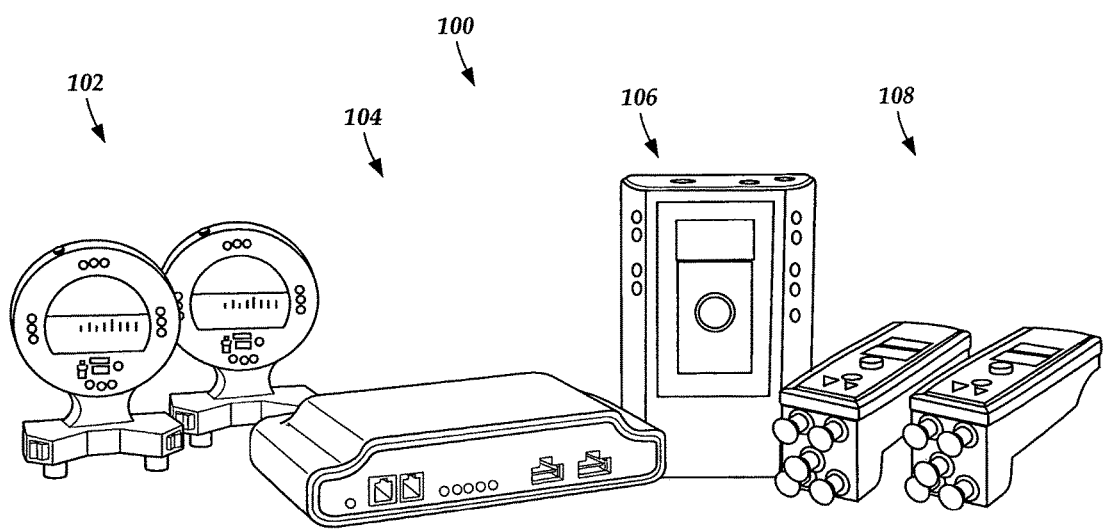
FIG. 1 is a schematic perspective view of one embodiment of a soft-tissue-injury diagnostic system, according to the invention.

The present invention is directed to medical diagnostic instrumentation. The present invention is also directed to systems and methods for evaluating soft-tissue-injury using surface electromyography or range-of-motion testing separately or in combination with one another.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Over the years, several types of medical diagnostic devices have been developed that measure one or more patient capabilities which may be helpful in evaluating soft-tissue injury. One such type of medical diagnostic device is a surface electromyograph ("sEMG"), which can be used for measuring the muscle tension of selected muscle groups of a patient, either while the patient performs various movements (e.g., a dynamic sEMG) or while a patient is at rest (e.g., a static sEMG). Another such type of medical diagnostic device is a range-of-motion tester ("ROM"), which can be used for measuring how far a patient can bend along a given joint. However, despite advancements in sEMG and ROM technologies, a tool for completely diagnosing soft-tissue injuries and assessing corresponding patient pain remains elusive.

As a result of the inability to reliably diagnose or assess soft-tissue injury, the healthcare system may experience a financial burden by misdiagnosing some types of patient injuries and consequently applying inappropriate therapies. Additionally, the insurance system and the court system may likewise experience a financial burden due to some people falsely claiming (or grossly exaggerating the extent of) soft-tissue injuries in order to receive money or other forms of consideration.

In at least some embodiments, a soft-tissue-injury diagnostic system ("diagnostic system") may be used to perform one or more diagnostic tests on a patient, either singularly or in combination, including an ROM test, a dynamic sEMG test, and a static sEMG test. In at least some embodiments, the diagnostic system also includes one or more video cameras. In at least some embodiments, multiple video cameras may be used to capture video (or photographs) of a patient's movements while undergoing one or more of the abovementioned tests. In at least some embodiments, results from one or more of the tests may be used by one or more medical practitioners to diagnose or assess soft-tissue injury.

FIG. 1 is a schematic perspective view of one embodiment of a diagnostic system 100. The diagnostic system 100 includes inclinometers 102 for performing an ROM test on a patient (testing how far the patient can bend), a hub 104, a dynamic sEMG control module ("sEMG module") 106 for use in performing a dynamic sEMG test on a patient (measuring action potentials along muscle groups as the patient performs various movements), and static sEMG scanners ("scanners") 108 for performing a static sEMG test on a patient (measuring action potentials along muscle groups as the patient maintains a given position).

In at least some embodiments, the inclinometers 102, the dynamic sEMG module 106, and the scanners 108 are in electrical communication with the hub 104. In some embodiments, one or more of the inclinometers 102, the dynamic sEMG module 106, and the scanners 108 are electrically coupled to the hub 104 by a wireless network, such as 3G. In other embodiments, one or more of the inclinometers 102, the dynamic sEMG module 106, and the scanners 108 are electrically coupled to the hub 104 by one or more conductors, such as wires.

Figure 2:
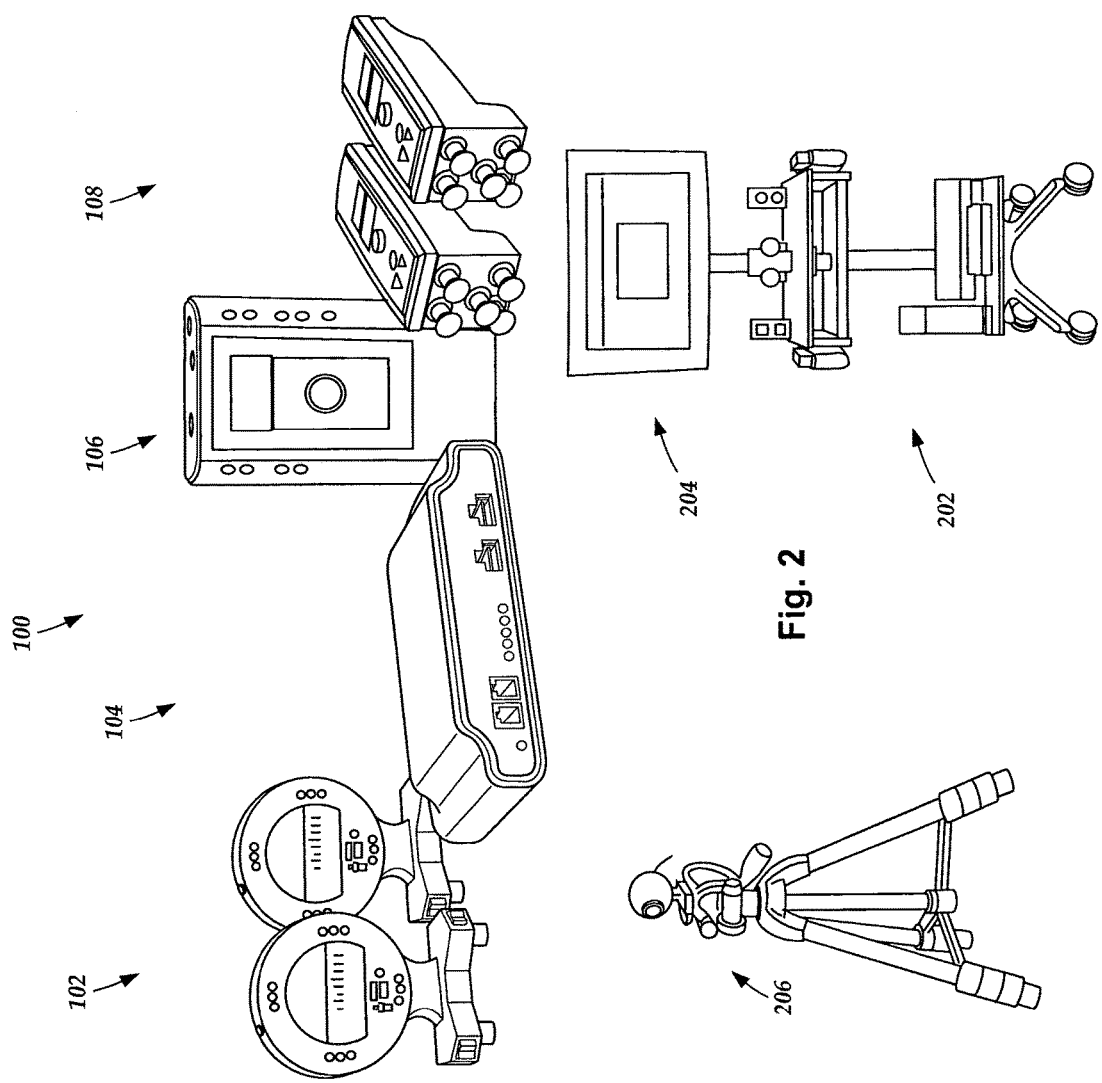
FIG. 2 is a schematic perspective view of another embodiment of the soft-tissue-injury diagnostic system shown in FIG. 1, according to the invention.

In at least some embodiments, the diagnostic system 100 also includes (as shown in FIG. 2) one or more processors 202, one or more visual displays 204, and one or more video cameras 206. In at least some embodiments, the hub 104 is electrically coupled to the one or more processors 202. In at least some embodiments, the one or more processors 202 receive and process input data from the inclinometers 102, the dynamic sEMG module 106, or the scanners 108 (via the hub 104) and display the results of the processed data on the one or more visual displays 204. In at least some embodiments, at least a portion of one or more of the ROM test, the dynamic sEMG test, or the static sEMG test are visually captured by the one or more video cameras 206.

In at least some embodiments, the diagnostic system 100 includes software or hardware for facilitating many different operations including, for example, linking the inclinometer 102, the dynamic sEMG module 106, or the scanners 108 to the hub 104, performing the ROM test, the dynamic sEMG, and the static sEMG, displaying the results of the ROM test, the dynamic sEMG, or the static sEMG, saving and backing-up testing data, and powering on or off the testing devices.

Figure 3:
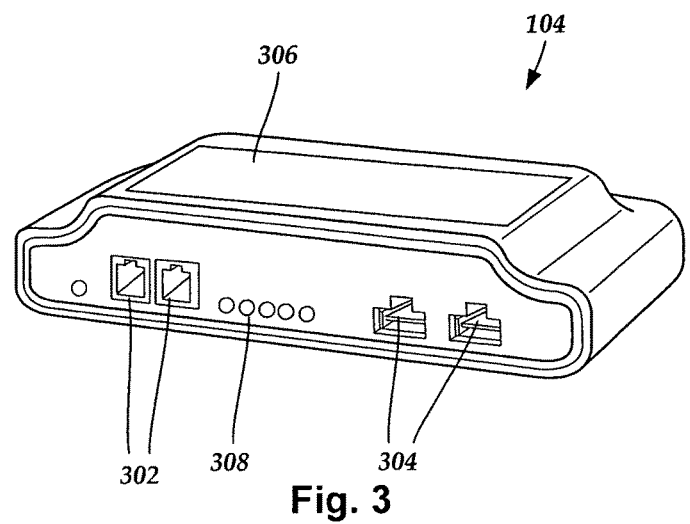
FIG. 3 is a schematic perspective view of one embodiment of a hub of the soft-tissue-injury diagnostic system shown in FIG. 1, according to the invention.

FIG. 3 is a schematic front view of the hub 104. In at least some embodiments, the hub 104 includes one or more inputs 302 for coupling the inclinometer 102, the dynamic sEMG module 106, or the scanners 108 to the hub 104. In at least some embodiments, the hub 104 also includes inputs 304 for one or more peripherals (e.g., a keyboard, a mouse, a monitor, a printer, a storage device, or the like). In at least some embodiments, the hub 104 includes one or more user interfaces 306 (e.g., displays, keypads, or the like). In at least some embodiments, the hub 104 includes one or more indicators 308, such as a power indicator, connectivity indicator, or the like. In at least some embodiments, multiple hubs 104 may be utilized, in parallel or in series. In at least some embodiments, the one or more hubs 104 receive and process input data from the inclinometers 102, the dynamic sEMG module 106, or the scanners 108 and display the results on a display, such as an LCD, coupled to (or disposed on) the hub 104. In at least some embodiments, the one or more hubs 104 include a keypad for inputting information.

Figure 4:
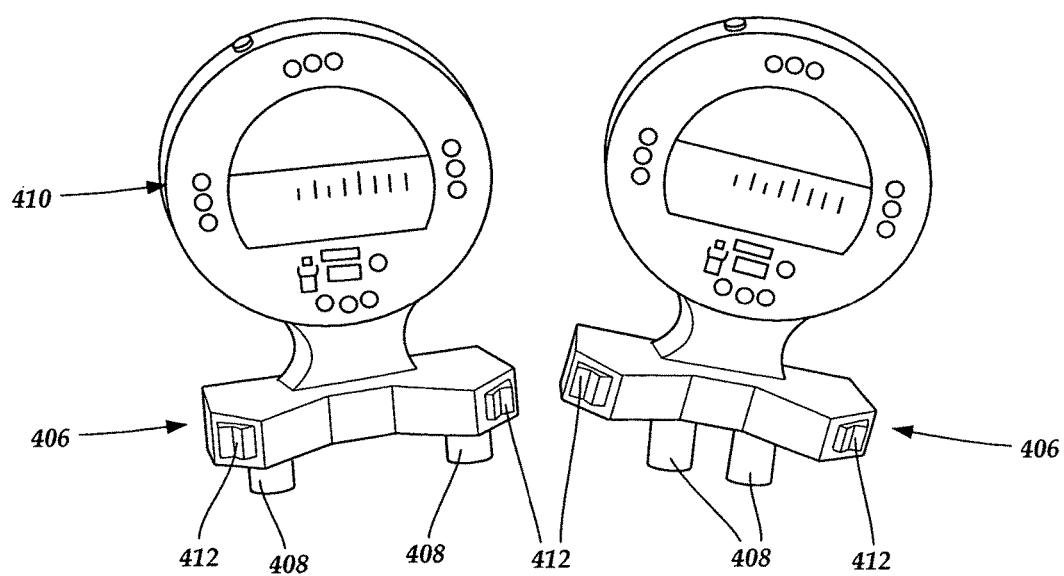
FIG. 4 is a schematic front view of one embodiment of inclinometers of the soft-tissue-injury diagnostic system shown in FIG. 1, the inclinometers including a main unit and an auxiliary unit, according to the invention.

FIG. 4 is a schematic front view of one embodiment of the inclinometers 102 of the diagnostic system 100. The inclinometers 102 includes a main unit 402 and an auxiliary unit 404. In at least some embodiments, the main unit 402 and the auxiliary unit 404 are each substantially disc-shaped with a coupled flat bottom surface 406 extending tangentially from a bottom portion of the discs. In at least one embodiment, the flat bottom surface 406 includes two or more feet 408. In at least some embodiments, the feet 408 are independently slidable along the flat bottom surface 406 such that the distance between the feet 408 may be adjusted.

In at least some embodiments, the main unit 402 and the auxiliary unit 404 each include a plurality of light-emitting diodes ("LEDs"), such as LEDs 410 positioned on the bodies of the main unit 402 and the auxiliary unit 404 to form degree markings. For example, the LEDs may be positioned to mark 0 degrees, 90 degrees, 180 degrees, and 270 degrees when the main unit 402 or the auxiliary unit 404 is placed in an upright position resting on the flat bottom surface 406. In at least some embodiments, the LEDs may be used by a user to determine a relative angle between the main unit 402 and the auxiliary unit 404 without needing to look at a computer display to obtain this information. In at least some embodiments, the LEDs may be used to mark the degrees of rotation between the main unit 402 and the auxiliary unit 404 based upon gravity.

In at least some embodiments, the main unit 402 and the auxiliary unit 404 use accelerometers. By using the LED degree markings and accelerometers, a user is able to use a true level (bubble-type level) to calibrate the inclinometers 102 to true center of the earth, and then have the ability to show, with LEDs, true zero with respect to gravity.

In at least some embodiments, the LEDs allow a user to see, by looking at the main unit 402 or the auxiliary unit 404, when the main unit 402 or the auxiliary unit 404 is at various degrees from earth center zero gravity. This allows the user to electronically provide a measurement without the use of a manual visual pendulum (which is a technique currently employed by some conventional devices). This may save time, and provide a more accurate reading as the angle data is stored by the hub 104 or the one or more processors 202, and does not require a human to calculate degrees.

In at least some embodiments, one or more LED-flashing systems may be implemented to convey to a user at what angle either the main unit 402 or the auxiliary unit 404 is at during performance of an ROM test. For example, when the LEDs are configured so that one or more LEDS mark 0 degrees, 90 degrees, 180 degrees, and 270 degrees, the LED(s) may provide feedback to the user as follows: when the main unit 402 or the auxiliary unit is at 0 degrees, for example, the one or more LEDs marking 0 degrees emit a green light. When the main unit 402 or the auxiliary unit 404 is rotated to 0 degrees minus 1 degree, the one or more LEDs marking 0 degrees emit a yellow light and flash at a rate of 1 time per second. When the main unit 402 or the auxiliary unit 404 are rotated to 0 degrees minus 2 degrees, the one or more LEDs marking 0 degrees emit a yellow light and flash at a rate of 2 times per second. In at least some embodiments, this continues on up to 5 degrees. When the main unit 402 or the auxiliary unit 404 are rotated to 0 degrees plus 1 degree, the one or more LEDs marking 0 degrees emit a red light or another color, and will flash with the same frequency as above, increasing at the same rate as the number of degrees increases from zero. So, for example, at 5 degrees, the one or more LEDs marking 0 degrees emit a red light and flash at a rate of 5 times per second.

In other embodiments, the main unit 402 or the auxiliary unit 404 each include 11 LEDs. In at least some embodiments, a plurality of colors are used. For example, the center may include 1 green LED. On either side at 1 degree increments there may be yellow LED's which indicate 1 degree increments under 0 degrees. On the other side of the 1 green LED there may be 5 red (or another color) LEDs which are spaced equally by 1 degree, and light up in order from the 1st to 5th LED indicating 1 to 5 degrees from center (0 degrees in this case). The 1 green LED in the center may emit light when the main unit 402 or the auxiliary unit 404 is held at 0 degrees compared to earth, and as the main unit 402 or the auxiliary unit 404 is moved away from 0 degrees (or any of the major markers (typically 0, 90, 180, 270), with the LED's lighting up in order as the 1-5 degrees is met from center.

In at least some embodiments, software associated with the ROM test utilizes voice signaling to facilitate operation of the inclinometers 102 or performance of an ROM test. For example, a voice signal may be output, via one or more speakers electrically coupled to the hub 104 or the one or more processors 202, the actual level in degrees in comparison to the center of the earth for one or both of the units 402 and 404 so that a user can focus on holding the main unit 402 or the auxiliary unit 404 against the patient and provide a more accurate reading, without dividing attention to attempt to read the values on a screen or on a mechanical device.

For example, when the main unit 402 or the auxiliary unit 404 is set up so that the top is at 0 degrees (is straight up and down), a voice signal may be emitted that says "zero degrees." In addition, the emitted voice signal may say "plus 1 degree," "plus two degrees," or the like, to mark the movement of the main unit 402 or the auxiliary unit 404 from center position. In at least some embodiments, voice signaling may be used to provide commands to a user of the inclinometers 102 before, during, or after a ROM test. For example, a voice signal may prompt the user when to instruct a patient to perform a given movement, when to record a marking (discussed below), or the like.

In at least some embodiments, the inclinometers 102 include one or more controllers 412 (e.g., buttons, switches, knobs, or the like) that may be used by a user during an ROM test to record a marking. For example, in at least some embodiments, the user may press a button during an ROM test to record a marking when a patient is at a neutral position, or when a patient is at a fully-flexed position. The recorded markings may be subsequently used to facilitate interpretation of a display of results from the ROM test. In at least some embodiments, two controllers 412 are positioned on each of the inclinometers 102. In at least some embodiments, the inclinometers 102 can be operated using either of the two controllers 412.

In at least some embodiments, the inclinometers 102 are powered by one or more batteries. In at least some embodiments, the inclinometers are automatically powered off after a given amount of time has elapsed without being used. In at least some embodiments, the inclinometers 102 are automatically powered off after the associated software has been powered off. In at least some embodiments, the inclinometers 102 are automatically powered off after an ROM test has been completed. In at least some embodiments, the inclinometers 102 include a master power switch which, when in one position, maintain the inclinometers 102 powered off.

In at least some embodiments, the inclinometer 102 is in electrical communication with the hub 104 and data created during the performance of an ROM test are input to the hub 104. In at least some embodiments, the data is processed by the hub 104 (or a plurality of hubs). In at least some embodiments, at least some of the data input to the hub 104 is output to the one or more electrically coupled processors 202 for further processing.

In at least some embodiments, the inclinometers 102 are positioned along a patient body portion that moves along a patient joint at one end of the body portion. The body portion can be any part(s) of the body, such as a limb, extending distally from a joint (e.g., head, neck, finger, hand, arm, forearm, waist, toe, ankle, knee, leg, or the like or combinations thereof). The inclinometers 102 may be positioned such that the main unit 402 is positioned against a patient joint and the auxiliary unit 404 is positioned distally from the joint along the movable body portion.

Figure 5:
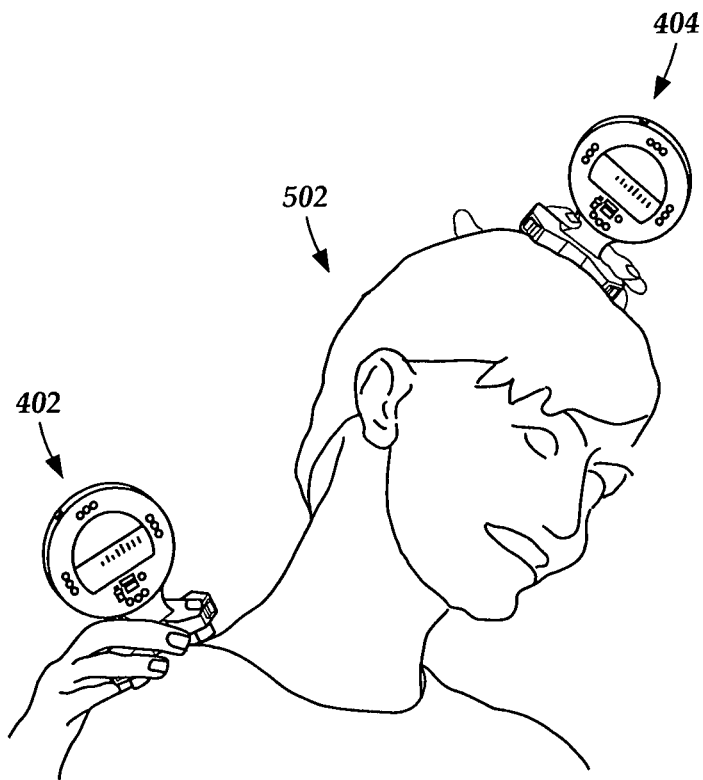
FIG. 5 is a schematic view of one embodiment of the inclinometers shown in FIG. 4 being used by a user to perform an ROM test on a patient, according to the invention.

FIG. 5 is a schematic view of one embodiment of the inclinometers 102 being used to perform an ROM test on a patient 502. In FIG. 5, a lateral flexion ROM test is being performed on the patient's cervical spine. It will be understood that this is just one of many different ROM tests that may be performed on a patient 502. In FIG. 5, the main unit 402 is positioned at the base of the neck, for example, and the auxiliary unit 404 on top of the head, a difference between the main unit 402 and the auxiliary unit 404 (in degrees compared with zero gravity ground) is measured as the patient moves from a neutral position to a fully-flexed position in a given direction (e.g., laterally flexed). As the patient 502 bends his or her head laterally, the difference between the two units 402 and 404 in degrees (main unit 402 minus auxiliary unit 404) provides the actual number of degrees which the patient 502 has flexed his or her neck. The main unit 402 and the auxiliary unit 404 may, therefore, be used to measure the range of motion as the hub 104 (or one or more coupled processors 202) is able to quickly and accurately measure both the main unit 402 and the auxiliary unit 404 simultaneously to measure the angle of movement. In at least some embodiments, the associated software remains idle until the patient 502 is in a final neutral posture.

In at least some embodiments, the feet 408 on the main unit 402 or the auxiliary unit 404 are adjustable. In at least some embodiments, at least one of the feet 408 slides along an axis separating the feet 408 (e.g., along an axis of the flat bottom surface 406), thereby increasing or decreasing the distance between the feet 408. In at least some embodiments, the adjustable feet 408 may be used to facilitate steady contact being made between the main unit 402 or the auxiliary unit 404 and the patient. For example, it may be the case that measuring the range of motion of one of the patient's fingers is more easily performed when the feet 408 are closer together than when measuring the range of motion of the patient's waist.

In at least some embodiments, the shape of the main unit 402 and the auxiliary unit 404 may also facilitate making steady contact with a patient. In at least some embodiments, a user may place hold of the main unit 402 or the auxiliary unit 404 between two of his or her fingers with his or her palm flat against the patient (as shown in FIG. 5) so as to steadily hold the main unit 402 or the auxiliary unit 404 in position while still being able to see the LEDs and use the control buttons 412 during performance of an ROM test.

Figure 6:
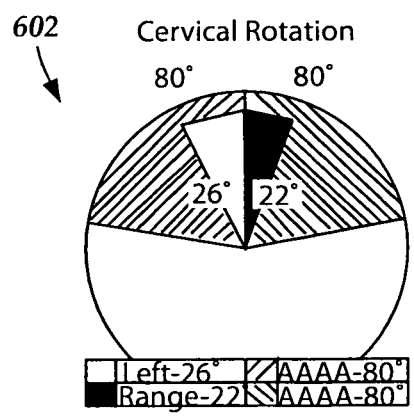
FIG. 6 is a schematic view of one embodiment of an exemplary result for an ROM test performed on a patient and displayable on a visual display, according to the invention.

FIG. 6 is a schematic view of one embodiment of an exemplary display 602 for an ROM test performed on the patient 502 and displayable on the one or more visual displays 204. Note that the exemplary display 602 of a ROM test can be displayed in many other different ways on the one or more visual displays 204. In at least some embodiments, the display 602 can be displayed on the hub 104 or other display electrically coupled to the hub 104 in lieu of, or in addition to, the one or more visual displays 204.

Figure 7:
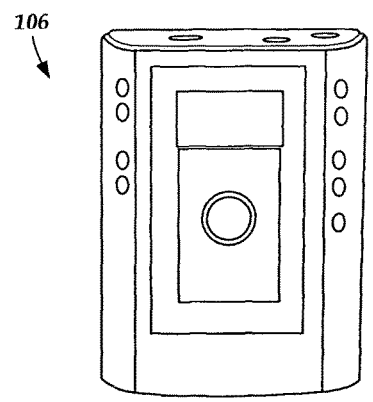
FIG. 7 is a schematic front view of one embodiment of an sEMG module of the soft-tissue-injury diagnostic system shown in FIG. 1, according to the invention.

FIG. 7 is a schematic front view of one embodiment of the dynamic sEMG module 106 of the diagnostic system 100. In at least some embodiments, the dynamic sEMG module 106 is configured and arranged for facilitating the performance of a dynamic sEMG test on a patient. In at least some embodiments, data collected during performance of the dynamic sEMG test is input to the hub 104 and processed by the hub 104 or by one or more processors 202. In at least some embodiments, the dynamic sEMG module 106 includes a master power switch (not shown) which, when in one position, maintain the dynamic sEMG module 106 powered off.

In at least some embodiments, the dynamic sEMG module 106 is configured and arranged to receive measuring electrodes coupled to a patient. In at least some embodiments, the dynamic sEMG module 106 is configured and arranged to receive up to sixteen measuring electrodes. The measuring electrodes coupled to the dynamic sEMG module 106 may be formed from many different conductive materials suitable for placement against the skin of a patient including, for example, gold, stainless steel, silver, silver chloride, and the like or combinations thereof. In at least some embodiments, multiple dynamic sEMG modules may be electrically coupled to one another or to the hub 104.

Figure 8:
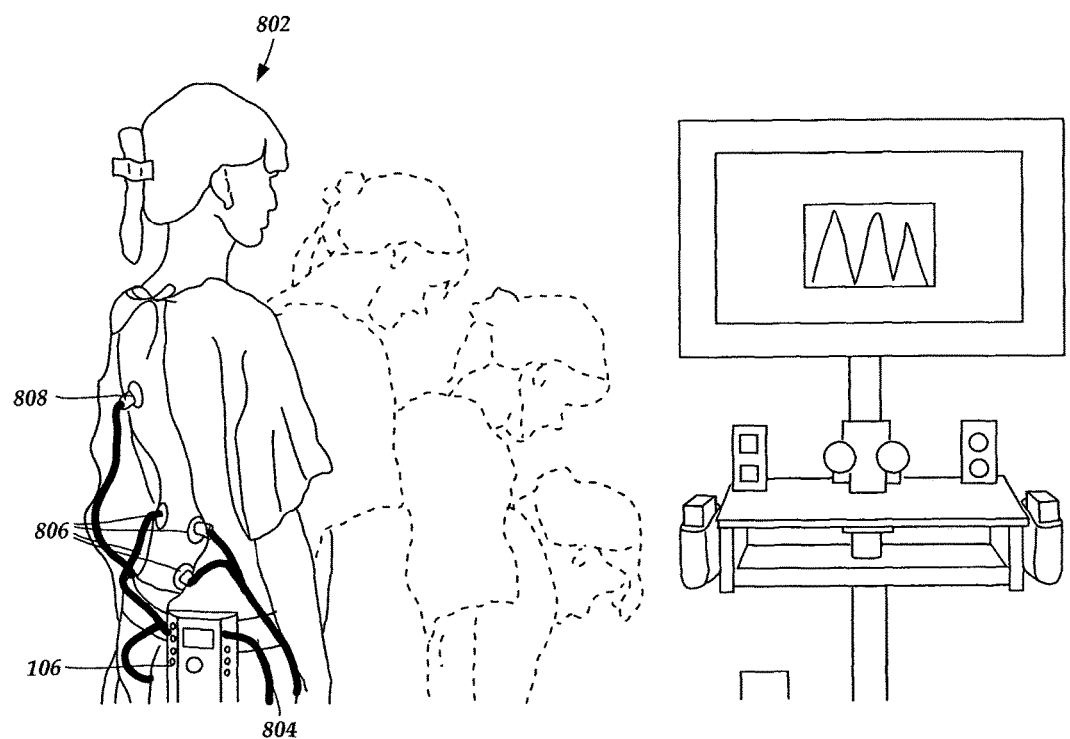
FIG. 8 is a schematic view of the dynamic sEMG module shown in FIG. 7 coupled to a patient via measuring electrodes while a dynamic sEMG test is performed on the patient, according to the invention.

FIG. 8 is a schematic view of a patient 802 performing a movement associated with a dynamic sEMG test. In FIG. 8, the dynamic sEMG module 106 is coupled to a strap 804 (e.g., a belt, or the like) being worn by the patient 802. In at least some embodiments, measuring electrodes 806 are attached to the patient 802 and electrically coupled to the dynamic sEMG module 106. The measuring electrodes 806 are positioned at various spinal levels determined by the muscle groups whose activity is to be measured during controlled patient movement. For example, the measuring electrodes 806 may be attached to the back of the patient 802 in lateral proximity to the spine at various spinal levels to measure the size and timing of action potentials as the patient moves in a manner that utilizes the muscles in proximity to the location of the attached measuring electrodes 806. In at least some embodiments, a ground 808 may also be used to couple the patient 802 to the dynamic sEMG module 106.

In FIG. 8, the patient 802 has measuring electrodes 806 attached to her back which measure the size and timing of action potentials along selected muscle groups during flexion and extension at her waist. In at least some embodiments, multiple dynamic sEMG modules 106 (each dynamic sEMG module 106 electrically coupled to multiple different measuring electrodes) may be used to perform multiple concurrent dynamic sEMG tests on a patient. In at least some embodiments, when multiple dynamic sEMG tests are performed on a patient, multiple results may be input to the hub 104.

Figure 9:
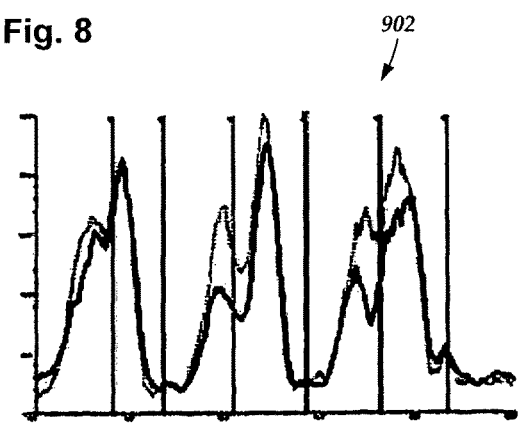
FIG. 9 is a schematic view of one embodiment of an exemplary result of a dynamic sEMG test performed on a patient, according to the invention.

FIG. 9 is a schematic view of one embodiment of an exemplary display 902 of a dynamic sEMG test performed on the patient 802. Note that exemplary display 902 of a dynamic sEMG test can be displayed in many other different ways on the one or more visual displays 204. In at least some embodiments, the exemplary display 902 is displayed on the hub 104 or a visual display electrically coupled to the hub 104.

Figure 10:
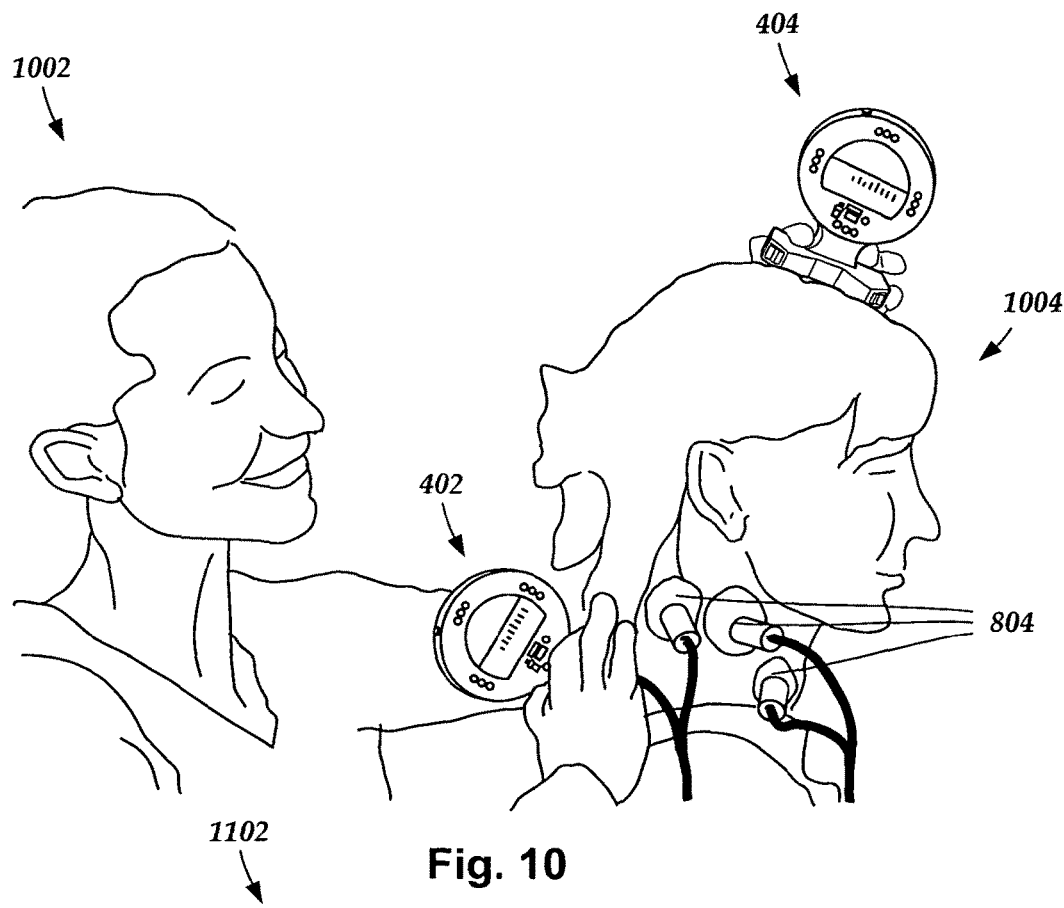
FIG. 10 is a schematic view of one embodiment of the inclinometers shown in FIG. 4 and the dynamic sEMG module shown in FIG. 7 being used to concurrently perform an ROM test and a dynamic sEMG test on a patient, according to the invention.

In at least some embodiments, an ROM test and one or more dynamic sEMG tests may be performed concurrently. FIG. 10 is a schematic view of one embodiment of a user 1002 concurrently performing an ROM test and a dynamic sEMG test on a patient 1004. The inclinometers 102 (ROM test) and the measuring electrodes 806 of the dynamic sEMG module 106 (dynamic sEMG test) are shown coupled to the patient 1004. In at least some embodiments, measuring muscle activity and range of motion concurrently may provide further insight into the nature and extent of patient injury. In at least some embodiments, data from both the ROM test and the dynamic sEMG test may be combined together in a single graphic display to show the timing, symmetry, and magnitude of the patient's muscle responses during patient movement. In at least some embodiments, combining an ROM test with a dynamic sEMG test may increase the accuracy of readings and also create results with increased reproducibility from conventional tests.

In at least some embodiments, the data for one or more of the motions from the ROM test may be arranged in a graphic which follows the American Medical Association ("AMA") guides for ROM, such as the pie graph result 602 shown in FIG. 6. Currently, the only known method to gather ROM data and generate impairment ratings based upon the AMA guides is to perform the ROM test separately from the dynamic sEMG. By performing the ROM test and dynamic sEMG tests concurrently and generating ROM data in the format required by the AMA guides, time and money may be saved. In at least some embodiments, when ROM data, after a selected number of trials of each motion, is not within the required variability allowed by the AMA guides, the software automatically informs the user that the ROM test in invalid, and may be performed again, thereby potentially saving additional time and money.

Figure 11:
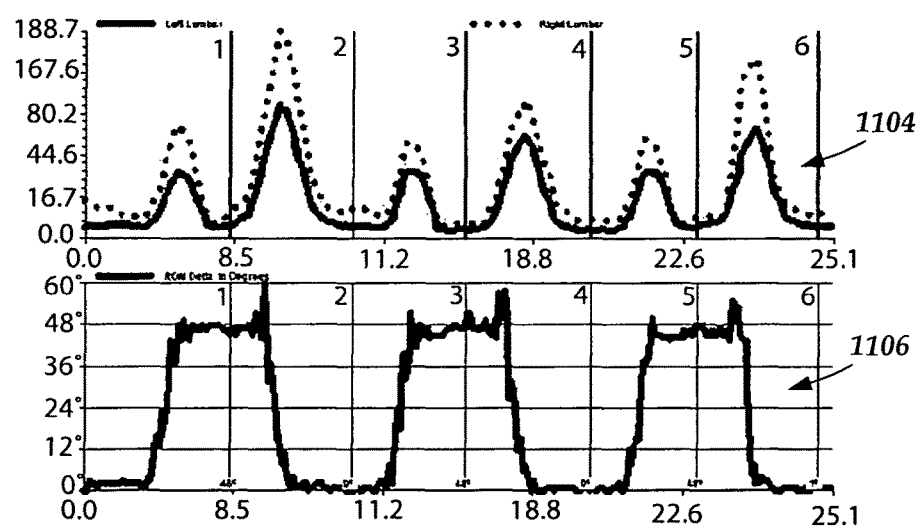
FIG. 11 is a schematic view of one embodiment of an exemplary result for an ROM test and a dynamic sEMG test performed concurrently on a patient and displayable together on a visual display, according to the invention.

FIG. 11 is a schematic view of one embodiment of an exemplary visual display 1102 showing results of a concurrently performed ROM test and dynamic sEMG test. In FIG. 11, the dynamic sEMG data 1104 is shown graphically on the top half of the visual display 1102 and the ROM data 1106 is shown graphically on the bottom half of the visual display 1102. The dynamic sEMG data 1104 and the ROM data 1106 are shown over time so that muscular activity of selected muscles can be seen visually during a corresponding performance of specific movements by the patient 1004. In at least some embodiments, timing, symmetry, and magnitude of the patient's muscle responses may be displayed. In at least some embodiments, such information may correspond with the nature and extent of patient injury.

Figure 12:
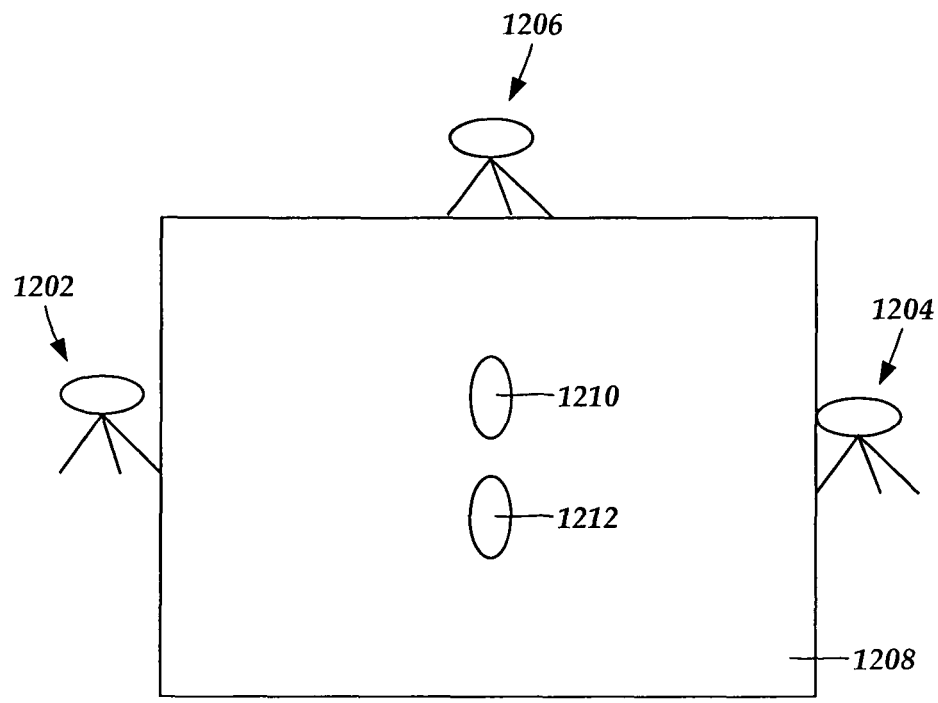
FIG. 12 is a schematic top view of one embodiment of an exemplary testing arrangement for capturing one or more static images or videos of a patient undergoing an ROM test or a dynamic sEMG test or both tests concurrently, according to the invention.

In at least some embodiments, further insight into the nature and extent of patient injury may be obtained by further including one or more video cameras, such as video camera 206, to capture one or more static images or, preferably, a video image of the performance of one or more of an ROM test and a dynamic sEMG test. FIG. 12 is a schematic top view of one embodiment of an exemplary testing arrangement for capturing one or more images or videos of a patient undergoing an ROM test and a dynamic sEMG test. In FIG. 12, three video cameras: 1202, 1204, and 1206, are placed around a mat 1208 that includes points 1210 and 1212 representing points for a patient to stand during performance of the ROM test and the dynamic sEMG test. In at least some embodiments, the video camera 1202 is positioned directly in front of a patient standing on points 1210 and 1212, while the video camera 1204 is positioned directly behind the patient, and while the video camera 1206 is positioned to one side of the patient.

In at least some embodiments, the addition of captured images or videos may be made available for review by one or more medical practitioners. In at least some embodiments, the data from one or more of the ROM test, dynamic sEMG test, and the videos (or static images) may be stored on the hub 104, one or more processors 202, or a storage device, and arranged so that one or more medical practitioners may use a slider to play back the patient's motion (for example, a forward flexion) and determine precisely the angle at which the patient has bent along with video of the patient's body showing the precise manner of movement. Moreover, similar testing may subsequently be performed on the same patient. Thus, comparison of two or more data sets may be performed to provide data for tracking patient progress over time.

Figure 13:
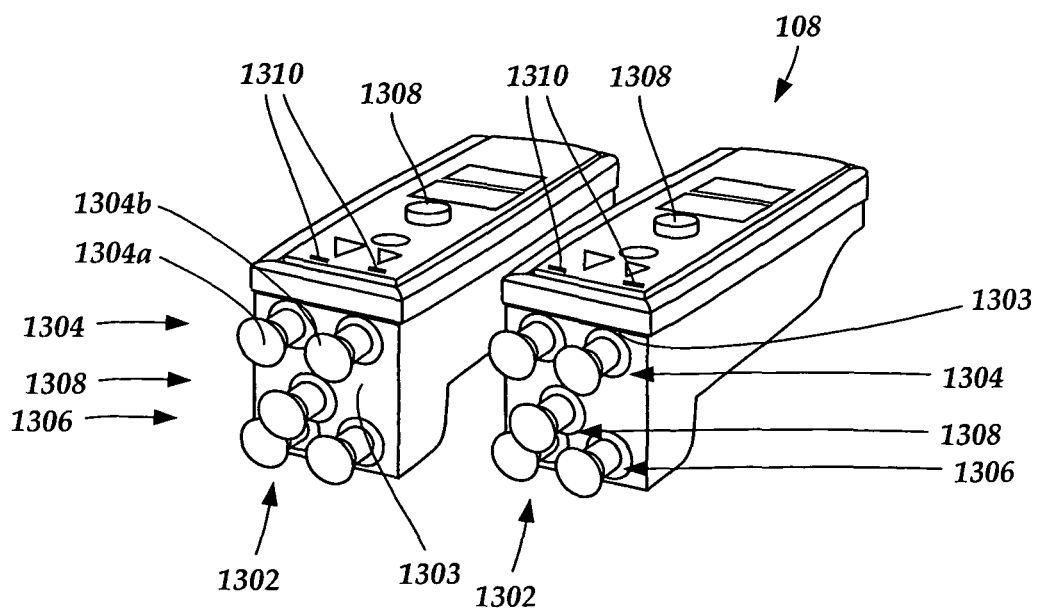
FIG. 13 is a schematic perspective view of one embodiment of a set of hand-held static sEMG scanners of the soft-tissue-injury diagnostic system shown in FIG. 1, according to the invention.

In at least some embodiments, the diagnostic system 100 includes scanners 108 for use by a user in administering a static sEMG test on a patient (measuring action potentials along selected muscle groups while the patient maintains a particular position). Sometimes a static sEMG test may involve a series of measurements taken during a set of successive placements of the scanners 108 against patient skin. FIG. 13 is a schematic perspective view of one embodiment of scanners 108 of the diagnostic system 100. The scanners 108 each include a plurality of measuring electrodes 1302 disposed on a front end 1303. In at least some embodiments, the measuring electrodes 1302 are arranged into sets, such as a first measuring electrode set 1304 and a second measuring electrode set 1306. The scanners 108 also include a ground 1308 disposed on the front end 1303.

In at least some embodiments, the scanners 108 are configured and arranged to be hand-held by a user during the performance of a static sEMG test. In at least some embodiments, the scanners 108 each include one or more controllers 1310 (e.g., buttons, switches, knobs, or the like). In at least some embodiments, a user of the scanners 108 may use the controllers 1310 to control progress during a static sEMG test without using a keypad, keyboard, or the like in between successive placements of the measuring electrodes 1304 against patient skin. In at least some embodiments, the scanner 108 includes one or more indicators 1312, such as one or more LEDs, which provide one or more indications to a user (e.g., battery level, on/off, connectivity, or the like) before, during, or after performance of a static sEMG test. In at least some embodiments, the scanners 108 include one or more gripping members (not shown) to facilitate gripping of the scanners 108 by the user 1602 while performing a static sEMG. For example, the scanners 108 may include one or more indentations configured and arranged to facilitate holding of the scanners 108 by the user 1602 during administration of a static sEMG test. In at least some embodiments, scanners 108 include a master power switch which, when in one position, maintain the scanners 108 powered off.

In at least some embodiments, the sets of measuring electrodes 1302 each include two electrodes, such as measuring electrodes 1304a and 1304b of the first measuring electrode set 1304. In at least some embodiments, the measuring electrodes within a set of measuring electrodes are horizontally spaced apart from one another on the front end 1303. In at least some embodiments, the sets of measuring electrodes are vertically spaced apart from one another. The ground 1308 can be disposed anywhere on the front end 108. In at least some embodiments, the ground 1308 is positioned vertically between the measuring electrode sets 1304 and 1306. In at least some embodiments, the ground 1308 is positioned horizontally between individual measuring electrodes within a set of measuring electrodes 1302.

In at least some embodiments, each set of measuring electrodes 1302 corresponds to a spinal level. Thus, the number of sets of measuring electrodes 1302 disposed on the scanner 108 may correspond to the number of spinal levels that can be simultaneously measured. In at least some embodiments, a user may place the measuring electrodes 1302 of the scanners 108 against a back of a patient in lateral proximity to the patient's spine at a desired level to measure action potentials. In at least some embodiments, the scanners 108 shown in FIG. 13 can be used to measure two spinal levels at a time for each placement of the scanners 108 against the patient, for example Cervical level 2 ("C2") and Cervical level 4 ("C4").

Any number of sets of measuring electrodes may be disposed on the scanner 108 including, for example, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or more sets of measuring electrodes. It will be understood that additional sets of measuring electrodes may be disposed on the scanner 108, as well.

In a least some embodiments, the scanners 108 communicate with the hub 104 (and, optionally, one or more processors 202, via the hub 104). In at least some embodiments, the scanners 108 are wireless. When the scanners 108 are wireless, a user and patient are not limited to either being positioned in the immediate vicinity of the hub 104 or creating a potential hazard by extending one or more conductors over a space where the conductors may present a hazard, such as potentially being tripped over. Consequently, wireless scanners 108 may be used, for example, at a screening (where a user is at a mall, health fair, car show, or the like) to go out into a crowd to test people without needing to entice people into a testing center. In at least some embodiments, the results of a static sEMG test may be shown in real-time on one or more visual displays 204. In at least some embodiments, data from a static sEMG may be transmitted at least thirty feet to the hub 104.

In at least some embodiments, the diagnostic system 100 may include multiple sets of scanners 108 so that multiple static sEMG tests may be performed on multiple patients while the data from each static sEMG test are input to the hub 104 (and, optionally, to one or more processors 202), processed, and the results output to one or more displays, such as the visual display 204. In at least some embodiments, the results of multiple static sEMG tests may be displayed concurrently on a single visual display 204. For example, the visual display 204 may include a split screen with static sEMG test results for two or more patients.

The measuring electrodes 1302 may be formed from many different conductive materials suitable for placement against the skin of a patient including, for example, gold, stainless steel, silver, silver chloride, and the like or combinations thereof. The ground 1308 may also be formed from many different conductive materials suitable for placement against the skin of a patient including, for example, gold, stainless steel, silver, silver chloride, and the like or combinations thereof. In at least some embodiments, the ground 1308 is formed from the same conductive material as the measuring electrodes 1302.

In at least some embodiments, the grounds 1308 of the scanners 108 are retractable in order to promote an improved contact between each ground 1308 and a patient when the scanners 108 are placed against the patient, and to also promote improved contact between the sets of measuring electrodes 1304 and 1306 and the patient, especially when the sets of measuring electrodes 1304 and 1306 are contacting curved portions of the patient, such as a patient's back.

Figure 14A:
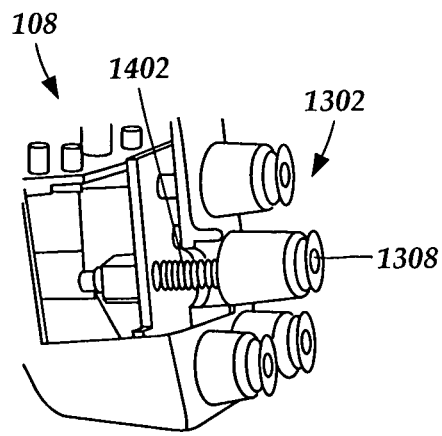
FIG. 14A is a schematic perspective view of one embodiment of one of the static sEMG scanners of FIG. 13 with a ground in an extended position and a portion of an outer casing of the static sEMG scanner removed, according to the invention.
Figure 14B:
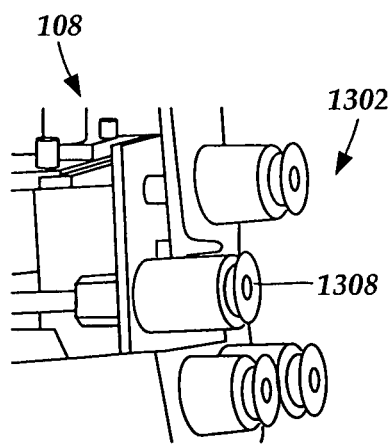
FIG. 14B is a schematic perspective view of one embodiment of one of the static sEMG scanners shown in FIG. 13 with a ground in a retracted position and a portion of an outer casing of the static sEMG scanner removed, according to the invention.

FIG. 14A is a schematic perspective view of one embodiment of one of the scanners 108 with the ground 1308 in an extended position and a portion of an outer casing of the scanner 108 removed, for clarity of illustration. In at least some embodiments, a spring, such as spring 1402, is positioned within the scanner 108 and used to provide the retractability of the ground 1308. It will be understood that any suitable type of spring may be implemented in the scanners 108 to provide retractability of the ground 1308 (e.g., tension, compression, torsional, coiled, flat, leaf, cantilever, hairspring, V-spring, or the like or combinations thereof). In at least some embodiments, by allowing the ground 1308 to retract, the scanner 108 may be better able to adjust to contours of the body, and allow the first and second sets 1304 and 1306, respectively, of the measuring electrodes 1302 to contact the skin of a patient, even when there is a curve in the patient's body which, without retractability would cause the ground 1308 to lift at least one of the sets 1304 and 1306, respectively, of the measuring electrodes 1302 off the skin of the patient. FIG. 14B is a schematic perspective view of one embodiment of one of the scanners 108 with the ground 1308 in a retracted position and a portion of an outer casing of the scanner 108 removed, for clarity of illustration.

In at least some embodiments, action potentials measured by the scanners 108 may be no greater than one milli-volt. Accordingly, ground loop protection and noise reduction may be important concerns. In at least some embodiments, noise is reduced, in part, by using wire links for each measuring electrode that are of similar length.

Figure 15:
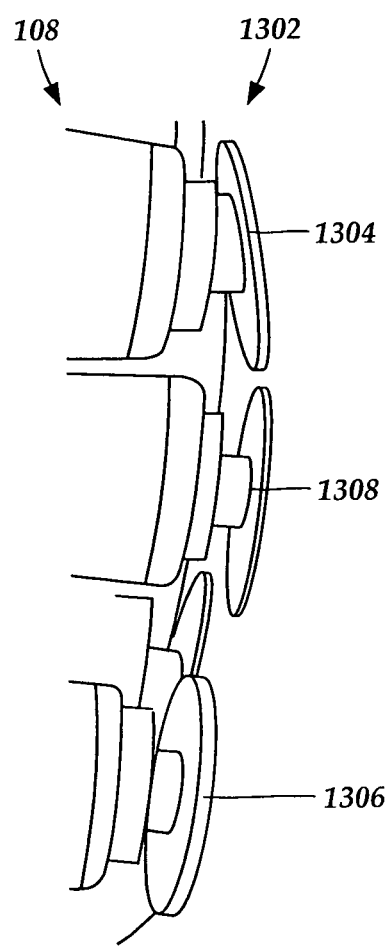
FIG. 15 is a schematic side view of one embodiment of one of the static sEMG scanners shown in FIG. 13 positioned against a patient such that the measuring electrodes are individually pivoted according patient contours, according to the invention.

In at least some embodiments, one or more of the measuring electrodes 1302 are pivotable to adapt to changes in body contours of a patient when, for example, the scanner 108 is pressed against the patient's body. FIG. 15 is a schematic side view of one embodiment of the measuring electrodes 1302 of one of the scanners 108 with the measuring electrodes 1304 and 1306 each pivoted at different angles from one another. In at least some embodiments, one or more of the measuring electrodes 1302 utilize an independent suspension system. In at least some embodiments, one or more of the measuring electrodes 1302 utilize a ball-and-socket system.

Figure 16:
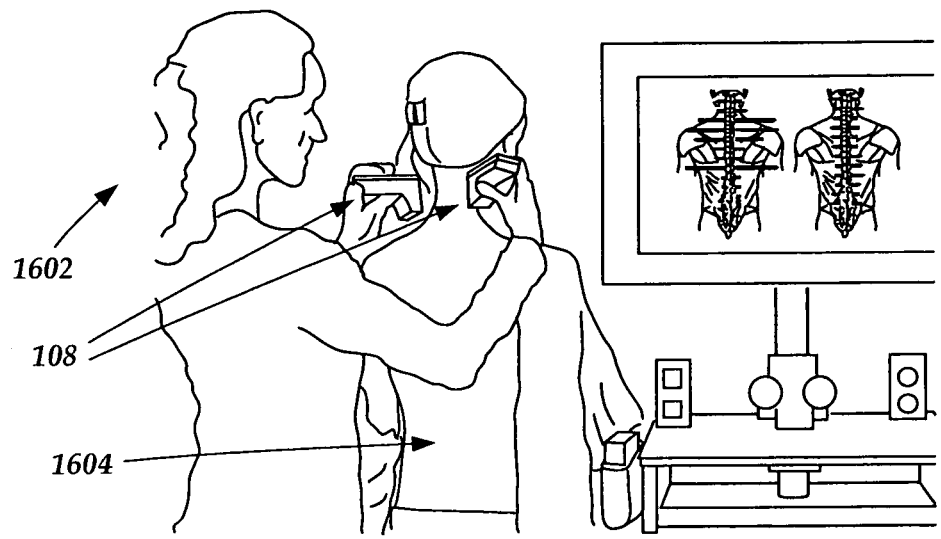
FIG. 16 is a schematic view of one embodiment of the static sEMG scanners shown in FIG. 13 being used by a user to perform a static sEMG test on a patient, according to the invention.

FIG. 16 is a schematic view of one embodiment of a user 1602 using the scanners 108 to perform a static sEMG test on a patient 1604. In at least some embodiments, each of the scanners 108 is positioned in lateral proximity to a spine of the patient 1604 at various levels of the spine. For example, in FIG. 16 the scanners 108 are positioned in lateral proximity to a cervical portion of the patient's spine. As discussed above, the scanners 108 each include two sets of measuring electrodes 1302. Thus, in FIG. 16 measurements can be taken concurrently at two spinal levels during each placement of the scanners 108 against the patient.

Over time, a series of measurements are obtained at different levels of the patient's spine. Action potentials of muscles are measured and the corresponding data is transferred to the hub 104 (and, optionally, one or more processors 202 via the hub 102), the data is processed, and results are displayed on one or more displays, such as the one or more visual displays 204.

In at least some embodiments, the scanners 108 are powered by one or more batteries. In at least some embodiments, during a static sEMG test the corresponding software executes a command to power off the scanners 108 for a period of time between successive placements to save battery power In at least some embodiments, during a static sEMG test the corresponding software executes a command to power on the scanners 108 when the scanners 108 are positioned against a patient, or when the controller 1301 is engaged. In at least some embodiments, during a static sEMG test the corresponding software executes a command to power off the scanners 108 after the one or more controllers 1308 are engaged.

In at least some embodiments, the hub 104 or the one or more processors 202 provide a prompt to alert the user 1602 when the scanners 108 are properly positioned against the patient 1604. In some embodiments, one or more of the positioning information and instructions for progressing through a static sEMG test is displayed on the one more visual displays 204. In other embodiments, the positioning information is provided via one or more voice commands.

Figure 17:
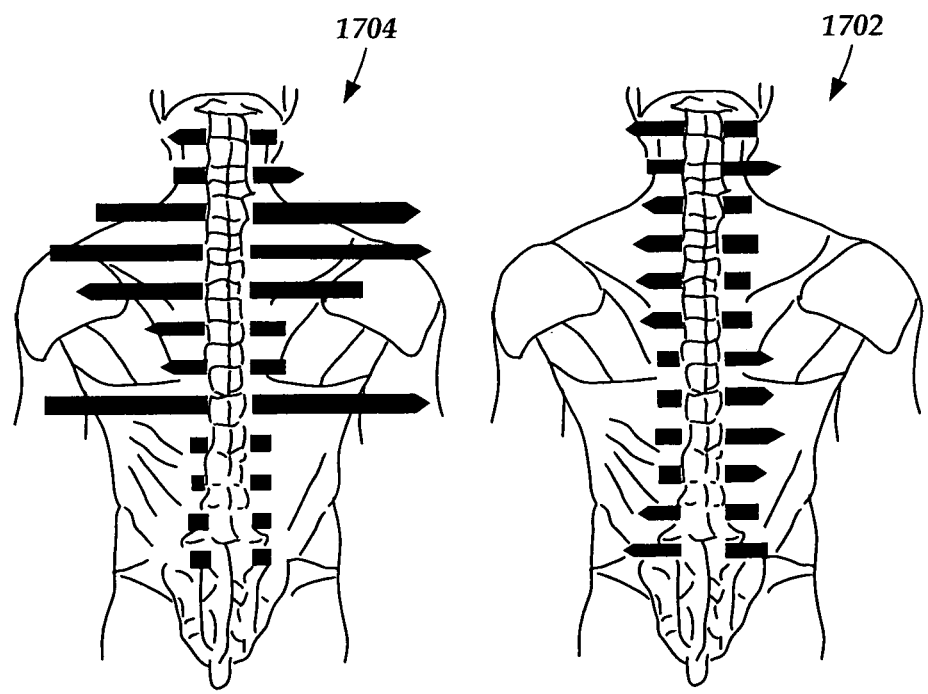
FIG. 17 is a schematic view of one embodiment of two exemplary results from a static sEMG test performed on a patient, according to the invention.

FIG. 17 is a schematic view of one embodiment of two exemplary results 1702 and 1704 for a static sEMG test performed on a patient. In at least some embodiments, the two results 1702 and 1704 are from a single patient. In at least some embodiments, the two results 1702 and 1704 are from two different patients. In at least some embodiments, one of the two results 1702 and 1704 is from a patient and the other result is a model result, such as an "ideal" result to compare against the patient's result.

As discussed above, the scanners 108 may include various numbers of sets of measuring electrodes. In at least some embodiments, more than two sets of measuring electrodes may be used. Additionally, in at least some embodiments additional grounds may also be used. In some embodiments, the measuring electrodes are coupled to hand-held scanners, such as the scanners 108. In at least some embodiments, measuring electrodes are coupled to scanners that may be self-standing or mounted to one or more planar surfaces, such as a wall.

Figure 18:
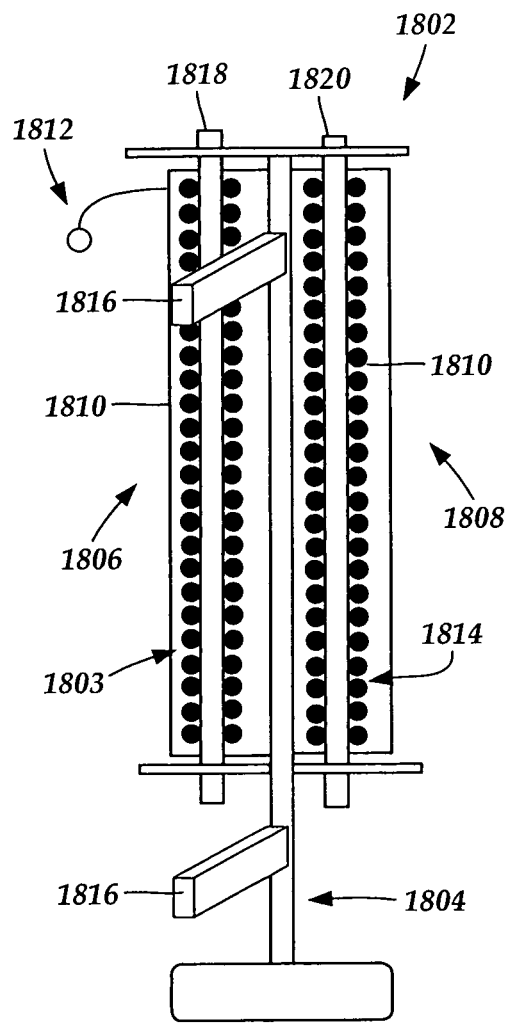
FIG. 18 is a schematic perspective view of one embodiment of a mountable static sEMG scanner of the soft-tissue-injury diagnostic system shown in FIG. 1, according to the invention.

FIG. 18 is a schematic perspective view of one embodiment of a static sEMG scanner 1802 with twenty-four sets of measuring electrodes 1803. The static sEMG scanner 1802 includes a base 1804, two columns 1806 and 1808 of sets of measuring electrodes 1803 mounted to one or more mounting boards 1810, and at least one ground 1812. Each column 1806 and 1808 includes a plurality of sets of measuring electrodes 1803, such as set 1814. In at least some embodiments, the static sEMG scanner 1802 is coupled to the hub 104.

In at least some embodiments, the measuring electrodes 1803 are retractable. Thus, in at least some embodiments when a patient contacts the measuring electrodes 1803, the measuring electrodes 1803 retract some amount of distance. In at least some embodiments, when the static sEMG scanner 1802 is mounted to a wall, the static sEMG scanner 1802 is positioned away from the wall far enough to accommodate the retraction of the measuring electrodes 1803 as the patient contacts the measuring electrodes 1803. In at least some embodiments, the static sEMG scanner 1802 includes one or more spacer bars 1816 to prevent one or more of the measuring electrodes 1803 from contacting a wall on which the static sEMG scanner 1802 is mounted when a patient is contacting (and consequently retracting) one or more of the measuring electrodes 1803.

In at least some embodiments, the measuring electrodes 1803 may be adjusted for improved contact against patient skin during a static sEMG test. In at least some embodiments, the two columns 1806 and 1808 of measuring electrodes 1803 are movably mounted such that they can be moved horizontally closer together or further apart from one another to improve measuring electrode 1803 contact with patients with spines of various widths. In at least some embodiments, the height from the floor of each of the columns 1806 and 1808 may be raised or lowered to improve measuring electrode 1803 contact with patients of different heights.

In at least some embodiments, a pivot extends between measuring electrodes 1803 of each set of measuring electrodes 1803 to improve contact with patients. In FIG. 18, the pivots are shown as two bars 1818 and 1820 extending vertically between measuring electrodes of each set of measuring electrodes 1803. In at least some embodiments, the measuring electrodes 1803 are mounted on a pliable substance, such as rubber, which facilitates a left/right pivot for each set of measuring electrodes 1803.

In at least some embodiments, accompanying software distinguishes measuring electrodes 1803 making contact with patient skin from measuring electrodes 1803 not making patient-skin contact. In at least some embodiments, the software can detect when action potential measurements from one or more of the measuring electrodes 1803 are zero (no patient contact). In at least some embodiments, a user can select the top and bottom measuring electrodes 1803 of the two columns 1806 and 1808 making contact with a patient from a display showing the measuring electrodes 1803. For example, the user can select that the top two sets of measuring electrodes 1803 of each of the mounting boards 1810 are to be ignored (e.g., when performing a static sEMG test on a particularly short patient). As another example, the user may select the top measuring electrode sets to be at the Cervical level 4 ("C4") of a patient and the bottom measuring electrode sets to be at Lumbar level 1 ("L1") of the patient, with the bottom six sets of measuring electrodes not contacting the patient.

Figure 19:
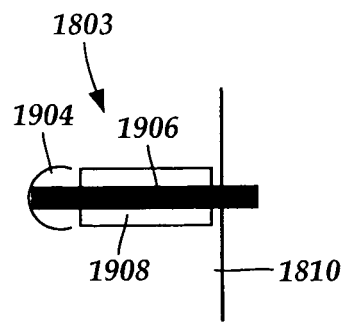
FIG. 19 is a schematic side view of one embodiment of a measuring electrode of the static sEMG scanner shown in FIG. 18, according to the invention.

FIG. 19 is a schematic side view of one embodiment of one of the measuring electrodes 1803 of the static sEMG scanner 1802. The measuring electrode 1803 includes a curved contact surface 1904 mounted to a conductive member 1906 which, in turn is mounted to the mounting board 1810. In at least some embodiments, the conductive member 1906 is coupled to a spring 1908. In at least some embodiments, the spring 1908 facilitates the retraction of the measuring electrode 1803 when a patient contacts the contact surface 1904 of the measuring electrode 1803. In one specific embodiment, the spring 1908 is configured and arranged so that the measuring electrode 1803 may be retracted up to twelve inches (approximately 30 cm).

Figure 20:
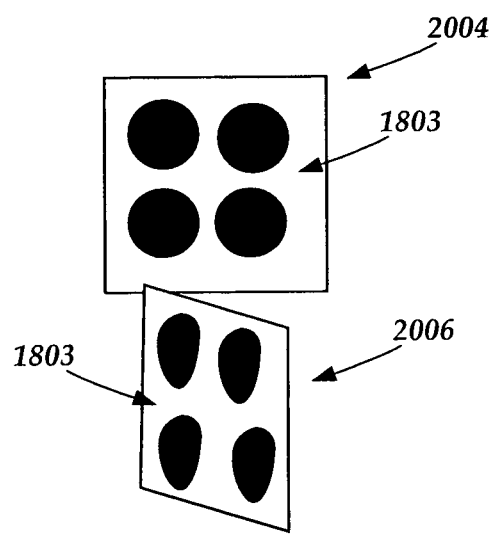
FIG. 20 is a schematic view of one embodiment of a set of four measuring electrodes of the static sEMG scanner shown in FIG. 18 in two positions, the second position horizontally pivoted from the first position, according to the invention.

FIG. 20 is a schematic view of one embodiment of four measuring electrodes 1803 in a first position 2004 and a second position 2006 that is horizontally pivoted from the first position 2004. In at least some embodiments, pivotable measuring electrodes may improve contact between the measuring electrodes 1803 and a patient when the patient is contacting the measuring electrodes 1803. In at least some embodiment, the measuring electrodes 1803 are pivoted about a pivot, such as one of the bars 1818 and 1820. In some embodiments, the measuring electrodes 1803 may pivot horizontally. In other embodiments, the measuring electrodes 1803 may pivot vertically. In other embodiments, the measuring electrodes 1803 may pivot along other axes other than a horizontal or a vertical axis. In other embodiments, patient contact is improved by using a pliable material, such as rubber, to form the non-contact surface of the measuring electrodes, the pliable material facilitating the bending of the measuring electrodes as needed when a patient is contacting the contact surface 1904 so as to improve contact.

Figure 21:
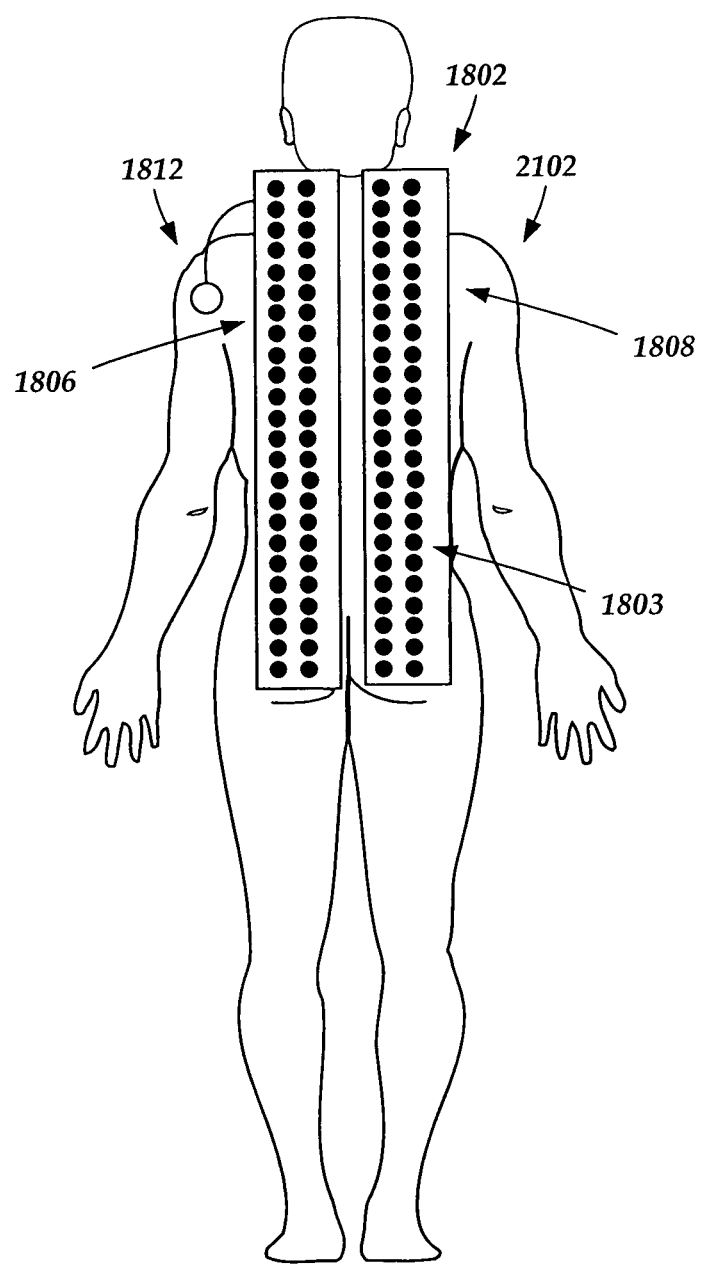
FIG. 21 is a schematic rear view of one embodiment of the static sEMG scanner shown in FIG. 18 aligned against a back of a human figure, according to the invention.

FIG. 21 is a schematic rear view of one embodiment of the static sEMG scanner 1802 aligned against a back of a human FIG. 2102. In FIG. 21 the two columns 1806 and 8108 of the measuring electrodes 1803 and the ground 1812 are contacting the back of the human FIG. 2102. In at least some embodiments, the two columns 1806 and 1808 of the measuring electrodes 803 are configured and arranged so that the measuring electrodes 1803 are contacting the back of the human FIG. 2102 in lateral proximity to the spine of the human FIG. 2102.

Figure 22:
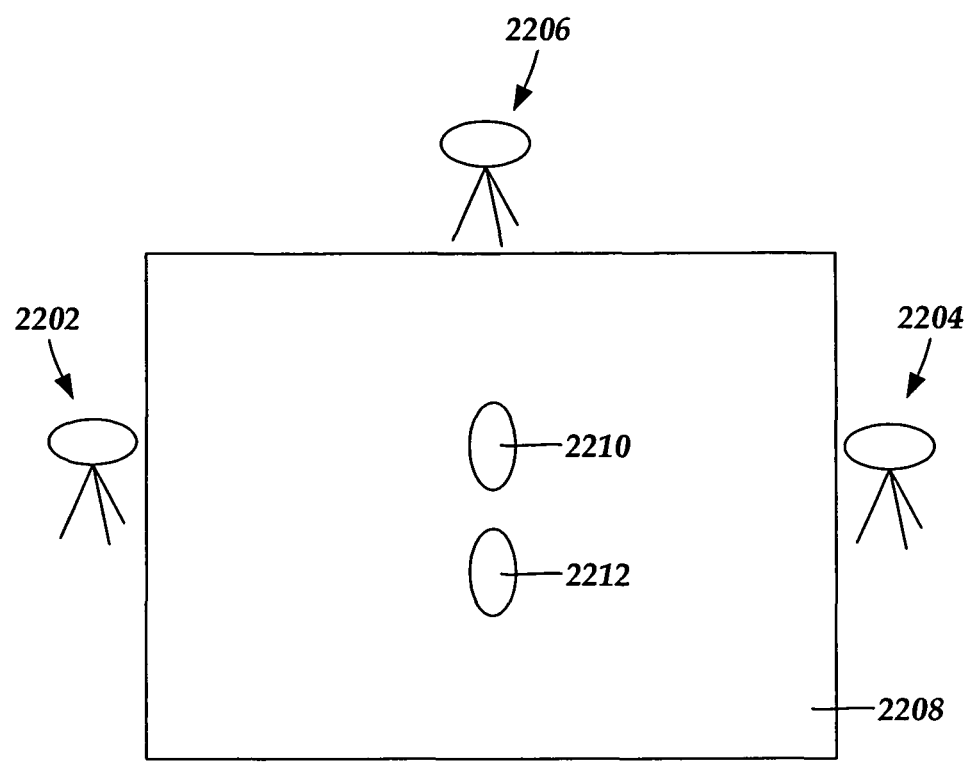
FIG. 22 is a schematic top view of one embodiment of an exemplary testing arrangement for capturing one or more images or videos of a patient while undergoing a static sEMG test, according to the invention.

In at least some embodiments, further insight into the nature and extent of patient injury may be obtained by further including one or more video cameras, such as video camera 206, to capture one or more images or videos of the performance of the static sEMG test. FIG. 22 is a schematic top view of one embodiment of an exemplary testing arrangement for generating images of the patient undergoing a static sEMG test. In FIG. 22, three video cameras: 2202, 2204, and 2206, are positioned around a mat 2208 that includes regions 2210 and 2212, representing a location for a patient to stand on during performance of the static sEMG test. In at least some embodiments, the video camera 2202 is positioned directly in front of a patient standing on the regions 2210 and 2212, while the video camera 2204 is positioned directly behind the patient, and while the video camera 2206 is positioned to one side of the patient. In at least some embodiments, at least one of one or more videos or one or more still images may be generated of the patient while the patient undergoes a static sEMG test.

In at least some embodiments, the addition of video (or one or more captured images) from one or more different angles may be made available for review by one or more medical practitioners. In at least some embodiments, the data from the static sEMG test and the one or more captured video (or static images) may be stored on the one or more processors 202 so that one or more medical practitioners may see precisely the positioning of the patient when the data was collected for a static sEMG test. Moreover, a similar test may be subsequently performed on the same patient in order to track patient progress over time.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A soft-tissue-injury diagnostic system for diagnosing soft tissue injury within a patient, the soft-tissue-injury diagnostic system comprising:

a set of hand-held inclinometers comprising a main unit and an auxiliary unit, the inclinometers configured and arranged for placement in proximity to two ends of a patient body portion that moves along a patient joint at one end of the body portion such that the main unit is positioned in proximity to the joint and the auxiliary unit is positioned along the patient body portion that moves along a patient joint, the inclinometers configured and arranged for measuring and recording angles formed between the main unit and the auxiliary unit during controlled patient movements of the joint, wherein the controlled patient movements of the joint comprise moving the joint between a first joint position and a second joint position that is different from the first joint position, wherein at least one controller is disposed on at least one of the main unit or the auxiliary unit, and wherein the at least one controller is configured and arranged for marking the recording of the measured angles at one or more of the first joint position and the second joint position when the at least one controller is actuated by a user, wherein a plurality of spaced-apart light-emitting diodes are disposed along each of the main unit and the auxiliary unit, and wherein the plurality of light-emitting diodes indicate degree markings and are configured and arranged to enable the user to view the measured angles between the main unit and the auxiliary unit during the controlled patient movements of the joint;

a static surface electromyograph ("sEMG") scanner, including:

at least one set of measuring electrodes that are electrically coupled to the static-sEMG scanner, the measuring electrodes configured in a housing and arranged for coupling to an exterior portion of the patient in lateral proximity to a plurality of levels of the patient's spine along the body portion that moves along the joint, the at least one set of measuring electrodes configured and for measuring action potentials along patient muscle groups beneath the measuring electrodes and transmitting the measured action potentials to the static sEMG scanner, and wherein the at least one set of measuring electrodes is non-retractable in the housing;

at least one ground electrode that is configured in the housing and arranged for placement against patient skin adjacent to the at least one set of measuring electrodes, wherein the at least one ground electrode is retractable in the housing independently of the at least one set of measuring electrodes to facilitate maintaining placement of the at least one ground electrode against patient skin during operation of the static sEMG scanner, wherein the at least one ground electrode is retractable to improve simultaneous contact with the patient skin between the static sEMG scanner and the at least one set of measuring electrodes, and wherein the at least one ground electrode is configured in an extended position beyond a surface of the housing and a position of the at least one set of measuring electrodes until the at least one ground electrode retracts from the extended position to a compressed position that is closer to the surface of the housing when the at least one set of measuring electrodes and the at least one ground electrode are placed against the patient skin; and a hub configured and arranged for receiving the data collected from the inclinometers and the static sEMG scanner during the controlled patient movements of the joint and processing the received data into at least one displayable image; and a visual display electrically coupled to the hub, the visual display configured and arranged for receiving and displaying the processed data from the hub.

2. The diagnostic system of claim 1, wherein the data collected from the inclinometers and the data collected from the static sEMG scanner are collected concurrently.

3. The diagnostic system of claim 1, further comprising at least one processor coupled to the hub, the at least one processor configured and arranged for providing additional processing power for processing the received data into at least one displayable image.

4. The diagnostic system of claim 1, wherein the inclinometers each comprise an accelerometer.

5. The diagnostic system of claim 1, wherein the inclinometers each are disc-shaped and have a flat bottom surface extending tangentially from a bottom portion of the inclinometer, the flat bottom surface of each inclinometer comprising two spaced-apart feet extending downward from the flat bottom surface, at least one of the two feet being adjustable along an axis of the flat bottom surface to adjust the amount of space between the two feet.

6. The diagnostic system of claim 1, wherein the plurality of light-emitting diodes are positioned along a periphery of each of the main unit and the auxiliary unit.

7. The diagnostic system of claim 1, further comprising at least one image-capturing device coupled to the hub, the at least one image-capturing device configured and arranged to capture at least one of a video or at least one static image of the patient performing the controlled patient movements of the joint.

8. The diagnostic system of claim 1, wherein the plurality of light-emitting diodes enable the user to determine the relative angle between the main unit and the auxiliary unit without looking at a computer display.

9. A static surface electromyography ("sEMG") scanner for measuring action potentials along selected muscle groups of a patient, the static sEMG scanner comprising:

at least two sets of measuring electrodes extending from the static sEMG scanner, the at least two sets of measuring electrodes are non-retractable and configured in a housing and arranged for placement against patient skin in lateral proximity to the patient's spine during operation of the static sEMG scanner, wherein each measuring electrode of the at least two sets of measuring electrodes is disposed a fixed distance apart from the remaining measuring electrodes of the at least two sets of measuring electrodes of the static sEMG scanner; and at least one ground electrode configured in the housing and arranged for placement against patient skin adjacent to the at least two sets of measuring electrodes, wherein the at least one ground electrode is retractable in the housing independently of the at least two sets of measuring electrodes to facilitate maintaining placement of the at least one ground electrode against patient skin during operation of the static sEMG scanner, wherein the at least two sets of measuring electrodes are non-retractable in the housing to improve simultaneous contact with the patient skin between the at least two sets of measuring electrodes and the at least one retractable ground electrode, and wherein the at least one ground electrode is configured in an extended position beyond a surface of the housing and a position of the two sets of measuring electrodes until the at least one ground electrode retracts from the extended position to a compressed position that is closer to the surface of the housing when the two sets of measuring electrodes and the at least one ground electrode are placed against the patient skin;

wherein the static sEMG scanner is configured and arranged to be held in a hand of a user during operation of the static sEMG scanner.

10. The static sEMG scanner of claim 9, wherein the at least two sets of measuring electrodes are each pivotable.

11. The static sEMG scanner of claim 9, wherein each set of the at least two sets of measuring electrodes comprises two measuring electrodes.

12. The static sEMG scanner of claim 9, wherein the at least two sets of measuring electrodes comprises a first set of measuring electrodes and a second set of measuring electrodes, and wherein the at least one ground electrode is disposed adjacent to and between the first set of measuring electrodes and the second set of measuring electrodes.

13. A method for diagnosing soft-tissue injury, the method comprising:

a) positioning a hand-held static surface electromyograph ("sEMG") scanner against patient skin at a first location, the static sEMG scanner comprising a housing that includes at least two sets of measuring electrodes and at least one ground electrode, each measuring electrode of the at least two sets of measuring electrodes disposed a fixed distance apart from the remaining measuring electrodes of the at least two sets of measuring electrodes of the static sEMG scanner, wherein the at least two sets of measuring electrodes adjacent to the at least one ground electrode are configured in the housing and arranged for contacting patient skin in lateral proximity to a plurality of adjacent levels of the patient's spine during operation of the static sEMG scanner, wherein the at least one ground electrode is retractable in the housing independently of the at least two sets of measuring electrodes to facilitate maintaining placement of the at least one ground electrode against patient skin during operation of the static sEMG scanner, wherein the at least two sets of measuring electrodes are non-retractable in the housing, wherein the at least one ground electrode is retractable to improve simultaneous contact with the patient skin between the at least one ground electrode and the two sets of non-retractable measuring electrodes, and wherein the at least one ground electrode is configured in an extended position beyond a surface of the housing and a position of the two sets of measuring electrodes until the at least one ground electrode retracts from the extended position to a compressed position that is closer to the surface of the housing when the two sets of measuring electrodes and the at least one ground electrode are placed against the patient skin;

b) measuring action potentials along patient muscle groups directly beneath the at least two sets of measuring electrodes;

c) transmitting data collected from the at least two sets of measuring electrodes to a hub for processing into at least one displayable image; and d) displaying the processed data from the hub on a visual display.

14. The method of claim 13, further comprising repositioning the static sEMG scanner such that the at least two sets of measuring electrodes adjacent to the at least one ground electrode contact patient skin in lateral proximity to a plurality of adjacent levels of the patient's spine at a second location along the spine and repeating elements b), c), and d).

15. The method of claim 14, wherein repositioning the static sEMG scanner such that the at least two sets of measuring electrodes adjacent to the at least one ground electrode contact patient skin in lateral proximity to a plurality of adjacent levels of the patient's spine at a second location along the spine comprises receiving an audible voice command to reposition the static sEMG scanner prior to repositioning the static sEMG scanner.

16. The method of claim 14, wherein repositioning the static sEMG scanner such that the at least two sets of measuring electrodes adjacent to the at least one ground electrode contact patient skin in lateral proximity to a plurality of adjacent levels of the patient's spine at a second location along the spine comprises powering off the static sEMG scanner during the repositioning of the static sEMG scanner.

17. A method for diagnosing soft-tissue injury, the method comprising:
positioning a set of hand-held inclinometers in proximity to two ends of a patient body portion that moves along a patient joint at one end of the body portion such that a main unit is positioned in proximity to the joint and an auxiliary unit is positioned along the patient body portion that moves along a patient joint;
coupling at least two sets of measuring electrodes in a housing to the patient in lateral proximity to a plurality of levels of the patient's spine along an exterior portion of the body portion that moves along the joint, wherein the at least two sets of measuring electrodes are electrically coupled to a static surface electromyograph ("sEMG") scanner, and wherein the at least two sets of measuring electrodes are non-retractable in the housing;
placing at least one ground electrode in the housing against patient skin adjacent to the at least two sets of measuring electrodes, wherein the at least one ground electrode is retractable in the housing independently of the at least two sets of measuring electrodes to facilitate maintaining placement of the at least one ground electrode against patient skin during operation of the static sEMG scanner, wherein the at least one ground electrode is retractable to improve simultaneous contact with the patient skin between the at least one ground electrode and the non-retractable measuring electrodes, and wherein the at least one ground electrode is configured in an extended position beyond a surface of the housing and a position of the measuring electrodes until the at least one ground electrode retracts from the extended position to a compressed position that is closer to the surface of the housing when the measuring electrodes and the at least one ground electrode are placed against the patient skin;
measuring and recording angles formed between the main unit and the auxiliary unit at the joint wherein the measured angles between the main unit and the auxiliary unit at the joint are displayable to a user;
marking the recording of the measured angles when at least one controller is disposed on at least one of the main unit or the auxiliary unit at the joint is actuated by the user;
measuring action potentials along patient muscle groups beneath the measuring electrodes of at the joint and transmitting the measured action potentials to the static sEMG scanner;
transmitting data collected from the inclinometers and the measuring electrodes to a hub for processing into at least one displayable image; and
displaying the processed data from the hub on a visual display.

18. The method of claim 17, wherein measuring and recording angles formed between the main unit and the auxiliary unit comprises actuating the at least one controller when the joint is positioned in at least one of a neutral position or a fully-flexed position.

19. A non-transitory computer-readable medium having processor-executable instructions for reading data from a range of motion ("ROM") device and a static surface electromyography ("sEMG") scanner device, the processor-executable instructions when installed and executed by one or more processors on a computer device enable the static sEMG scanner device to perform actions, comprising:
processing angles measured and recorded between a main unit and an auxiliary unit of the ROM device at a joint at one end of a patient body portion, wherein the main unit is positioned in proximity to the joint and the auxiliary unit positioned along the patient body portion that moves along a patient joint, wherein the measured angles between the main unit and the auxiliary unit are displayable to a user;
marking the recording of the measured angles when at least one controller disposed on at least one of the main unit or the auxiliary unit at the joint is actuated by the user;
processing action potentials measured along patient muscle groups beneath measuring electrodes of the static sEMG scanner device at the joint, the measuring electrodes are configured in a housing and arranged to be coupled to patient skin in lateral proximity to a plurality of levels of the patient's spine along the body portion, wherein the measuring electrodes are non-retractable in the housing;
receiving a ground signal from at least one ground electrode in the housing against patient skin adjacent to the measuring electrodes, wherein the at least one ground electrode is retractable in the housing independently of the non-retractable measuring electrodes to facilitate maintaining placement of the at least one ground electrode against patient skin during operation of the static sEMG scanner device, wherein the at least one ground electrode is retractable to improve simultaneous contact with the patient skin between the at least one ground electrode and the non-retractable measuring electrodes, and wherein the at least one ground electrode is configured in an extended position beyond a surface of the housing and a position of the measuring electrodes until the at least one ground electrode retracts from the extended position to a compressed position that is closer to the surface of the housing when the measuring electrodes and the at least one ground electrode are placed against the patient skin; and
displaying the processed data on a visual display.

20. A soft-tissue injury diagnostic device comprising:
a range of motion ("ROM") device and a static surface electromyography ("sEMG") scanner device coupled to a hub; and a processor in communication with the hub, wherein the processor executes processor-readable instructions that enable actions, including:

processing angles measured and recorded between a main unit and an auxiliary unit of the ROM device of a joint at one end of a patient body portion, wherein the main unit positioned in proximity to the joint and the auxiliary unit is positioned along the patient body portion that moves along a patient joint, wherein the measured angles between the main unit and the auxiliary unit of the joint are displayable to a user;

marking the recording of the measured angles when at least one controller disposed on at least one of the main unit or the auxiliary unit is actuated by the user;

processing action potentials measured along patient muscle groups beneath measuring electrodes of the static sEMG scanner device, wherein the measuring electrodes are configured in a housing and arranged to be coupled to patient skin in lateral proximity to a plurality of levels of the patient's spine along the body portion, wherein the measuring electrodes are non-retractable in the housing;

receiving a ground signal from at least one ground electrode in the housing placed against patient skin adjacent to the measuring electrodes, wherein the at least one ground electrode is retractable in the housing independently of the measuring electrodes to facilitate maintaining placement of the at least one ground electrode against patient skin during operation of the static sEMG scanner device, wherein the at least one ground electrode is retractable to improve simultaneous contact with the patient skin between the at least one ground electrode and the non-retractable measuring electrodes, and wherein the at least one ground electrode is configured in an extended position beyond a surface of the housing and a position of the measuring electrodes until the at least one ground electrode retracts from the extended position to a compressed position that is closer to the surface of the housing when the measuring electrodes and the at least one ground electrode are placed against the patient skin; and displaying the processed data on a visual display.

* * * * *

UNITED STATES PATENT AND TRADEMARK OFFICE
CERTIFICATE OF CORRECTION

PATENT NO. : 9,808,172 B2
APPLICATION NO. : 12/455385
DATED : November 7, 2017
INVENTOR(S) : Marcarian Page 1 of 1

It is certified that error appears in the above-identified patent and that said Letters Patent is hereby corrected as shown below:

In the Specification

In Column 1, Line 10, delete "Application," and insert -- Application --, therefor.

In Column 11, Line 16, delete "front end 108." and insert -- front end 1303. --, therefor.

In Column 11, Line 43, delete "a least" and insert -- at least --, therefor.

In Column 13, Line 13, delete "hub 102)," and insert -- hub 104), --, therefor.

In Column 13, Line 24, delete "controller 1301" and insert -- controller 1310 --, therefor.

In Column 13, Lines 27-28, delete "controllers 1308" and insert -- controllers 1310 --, therefor.

In the Claims

In Column 17, Line 2, in Claim 1, delete "skin; and" and insert -- skin; --, therefor.

Signed and Sealed this
Eighteenth Day of June, 2019

Andrei Iancu
*Director of the United States Patent and Trademark Office*